United States Patent [19]

Sugie

[11] Patent Number: 4,985,053
[45] Date of Patent: Jan. 15, 1991

[54] GAS SEPARATION MEMBRANE

[75] Inventor: Kiyoshi Sugie, Iwakuni, Japan

[73] Assignee: Agency of Industrial Science and Technology, Tokyo, Japan

[21] Appl. No.: 483,281

[22] Filed: Feb. 21, 1990

Related U.S. Application Data

[63] Continuation of Ser. No. 234,084, Aug. 19, 1988, abandoned.

[30] Foreign Application Priority Data

Aug. 22, 1987 [JP] Japan ................. 62-207417
Feb. 6, 1988 [JP] Japan ................. 63-24934

[51] Int. Cl.$^5$ ................. B01D 53/22; B01D 71/36
[52] U.S. Cl. ................. 55/158; 55/16; 55/68; 423/219
[58] Field of Search ................. 55/16, 68, 158; 423/219, 246, 579

[56] References Cited

U.S. PATENT DOCUMENTS

| | | | |
|---|---|---|---|
| 4,011,306 | 3/1977 | Fox, Jr. ................. | 423/579 |
| 4,032,617 | 6/1977 | Gay ................. | 423/219 |
| 4,047,908 | 9/1977 | Steigelmann et al. ................. | 55/158 |
| 4,087,372 | 5/1978 | Saitoh et al. ................. | 55/68 X |
| 4,091,073 | 5/1978 | Winkler ................. | 55/68 X |
| 4,091,822 | 5/1978 | Ihrig et al. ................. | 55/68 X |
| 4,198,792 | 4/1980 | Christensen et al. ................. | 55/68 X |
| 4,323,543 | 4/1982 | McAuliffe et al. ................. | 423/219 |
| 4,457,898 | 7/1984 | Hill et al. ................. | 423/219 |
| 4,516,984 | 5/1985 | Warner et al. ................. | 55/158 X |
| 4,542,010 | 9/1985 | Roman et al. ................. | 55/16 X |
| 4,584,359 | 4/1986 | Sterzel et al. ................. | 55/158 X |
| 4,609,383 | 9/1986 | Bonaventura et al. ................. | 55/16 |
| 4,627,859 | 12/1986 | Zupancic et al. ................. | 55/158 |
| 4,654,053 | 3/1987 | Sievers et al. ................. | 55/68 |
| 4,668,255 | 5/1987 | Govind ................. | 55/68 X |
| 4,680,037 | 7/1987 | Ramprasad et al. ................. | 55/16 |
| 4,705,544 | 11/1987 | Okita et al. ................. | 55/16 X |
| 4,713,091 | 12/1987 | Govind ................. | 55/68 X |
| 4,735,634 | 4/1988 | Norman et al. ................. | 55/16 |
| 4,766,229 | 8/1988 | Kobayashi et al. ................. | 55/68 X |

FOREIGN PATENT DOCUMENTS 0098731 1/1984 European Pat. Off.
0154247 9/1985 European Pat. Off.
0176986 4/1986 European Pat. Off.
54-013476 5/1979 Japan.

OTHER PUBLICATIONS

Nishide et al., *Chemistry Letters*, pp. 43–46, 1986, The Chemical Society of Japan.
Johnson, Bruce M. et al., *Journal of Membrane Science*, 6036, 31(1987), Apr., No. 1, Amsterdam, The Netherlands.

*Primary Examiner*—Robert Spitzer
*Attorney, Agent, or Firm*—Sherman and Shalloway

[57] ABSTRACT

A gas separation film comprising a perm-selective layer which is formed by reaction in situ of a Schiff base metal complex compound represented by the following formula (I)

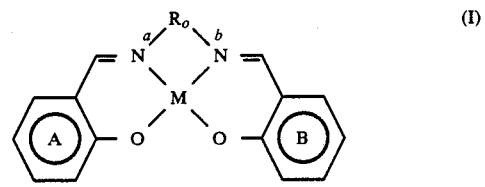

wherein rings A and B each represent an o-phenylene or o-naphthylene group which may be substituted by at least one group selected from the class consisting of halogen atoms and groups of the formula —X—R in which R represents a saturated or unsaturated aliphatic hydrocarbon group having not more than 22 carbon atoms and X represents a direct bond or a binding member between R and ring A or B, selected from the class consisting of —O—, —COO—, —NHCO— and —S—, $R_o$ represents a hydrocarbon group having not more than 6 carbon atoms in which adjacent carbon atoms or adjacent carbon atoms via one carbon atom are bound to bonds a and b, and M represents a metal selected from the group consisting of Fe, Co, Cu, Ni, Mn, Cr and Zn, with a polymeric ligand.

17 Claims, No Drawings

GAS SEPARATION MEMBRANE

This application is a continuation of application Ser. No. 07/234,084 filed Aug. 19, 1988, now abandoned.

This invention relates to a novel gas separation film having a permselective layer which is formed by reaction of a specific Schiff base metal complex compound with a polymeric ligand. The film is especially useful as an oxygen separation film.

In recent years, much interest has been aroused in a process of membrane separation which concentrates a specific component of a gaseous mixture, and separates it from the mixture, by utilizing the permselectivity of a membrane, and research and development work on it has been actively done. In handling a gaseous mixture, this membrane separation process is expected to be useful because it does not involve phase change in the separation process and contributes much to energy saving. Attempts at industrial application of this process are under way.

Many attempts have previously been made to separate gaseous mixtures using membranes composed of a synthetic polymer. But the ability of these membranes to separate gases selectively is not sufficient and they have not gained commercial acceptance.

In order to increase selectivity of the membranes, attempts have been made to introduce metal complexes which selectively coordinate with gases into the membranes. For example, Japanese Patent Publication No. 13476/1979 discloses a process for producing a membranous material composed of a polymeric metal complex. This membranous material: however, has the defect that if the proportion of the complex introduced is increased, gelation occurs and film-formability is reduced.

Tsuchida et al. showed that a membrane composed of a blend of a polymer with a metal complex or a polymeric complex membrane containing a polymeric ligand exhibit high selectivity (E. Tsuchida et al., Chemistry Letters, 1986, 43). In these membranes, it is difficult to increase the content of the complex because it causes gellation. Furthermore, in order to obtain high selectivity, the supply pressure should be lowered, and the permeation velocity decreases. These are unsatisfactory in practical application.

The present inventors have made extensive investigations in order to obtain a permselective membrane having both high permeability and high selectivity. These investigations have led to the discovery that a membrane having a permselective layer formed by the reaction of a Schiff base metal complex with a polymeric ligand has excellent selectivity and high permeability.

A first object of this invention is to provide a gas separation film having the excellent ability to absorb and desorb a gas reversibly and being free from degradation.

A second object of this invention is to provide an excellent oxygen separation film.

A third object of this invention is to provide a process for producing the gas separation film by reaction in situ.

In accordance with this invention, these objects are achieved by a gas separation film comprising a permselective layer which is formed in situ by reaction of a Schiff base metal complex compound represented by the following formula (I)

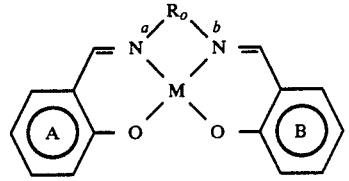

wherein rings A and B each represent an o-phenylene or o-naphthylene group which may be substituted by at least one group selected from the class consisting of halogen atoms and groups of the formula —X—R in which R represents a saturated or unsaturated aliphatic hydrocarbon group having not more than 22 carbon atoms and X represents a direct bond or a binding member between R and ring A or B, selected from the class consisting of —O—, —COO—, —NHCO— and —S—, $R_o$ represents a hydrocarbon group having not more than 6 carbon atoms in which adjacent carbon atoms or adjacent carbon atoms via one carbon atom are bound to bonds a and b, and M represents a metal selected from the group consisting of Fe, Co, Cu, Ni, Mn, Cr and Zn, with a polymeric ligand.

In the present invention, the term "gas separation film" means a film which can separate a specific component from a gaseous mixture containing it. Specifically, the gas separation film includes a film which can separate oxygen gas from an oxygen gas-containing gaseous mixture such as air, and a film which can separate CO gas from a CO gas-containing gaseous mixture such as water gas.

The term "permselective layer" means an ultrathin film (layer) to which the selectivity of the gas separation film is due for the most part.

The above ultrathin film is formed in situ by reacting a Schiff base metal complex compound represented by formula (I)

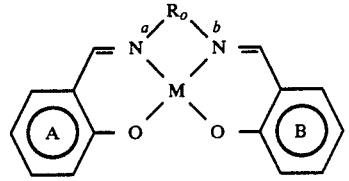

wherein rings A and B, $R_o$ and M are as defined above,
with a polymeric ligand.

Rings A and B in formula (1) each represent an o-phenylene or o-naphthyene group which may be substituted by at least one group selected from the class consisting of halogen atoms and groups of the formula —X—R in which R represents a saturated or unsaturated aliphatic hydrocarbon group having not more than 22 carbon atoms and X represents a direct bond or a binding member between R and ring A or B, selected from the class consisting of —O—, —COO—, —NHCO— and —S—. The saturated or unsaturated alkyl group (R) is an alkyl, alkenyl or alkynyl group having not more than 22 carbon atoms. Specific examples of the alkyl group are linear or branched alkyl groups such as methyl, ethyl, propyl, isopropyl, butyl, isobutyl, tert-butyl, hexyl, octyl, 3-ethylhexyl, tetradecyl, pentadecyl, hexadecyl, heptadecyl, octadecyl, and docosyl groups; alkenyl groups such as vinyl, allyl, cis-9-hexadecenyl, and cis-9-cis-12-octadecadienyl groups; and alkynyl groups such as propargyl and octadeca-1-,12-diyl groups. These examples are not limitative, however The hydrocarbon groups are preferably lower, and lower alkyl groups are especially preferred. The term "lower", as used herein to qualify groups or compounds, means that the groups or compounds so qualified have not more than 6 carbon atoms, preferably not more than 4 carbon atoms.

Rings A and B are preferably an o-phenylene or o-naphthylene group having no substituent or having a methoxy group as a substituent. An o-phenylene group having no substituent is especially preferred.

$R_o$ represents a linear or cyclic hydrocarbon group having not more than 6 carbon atoms, preferably not more than 4 carbon atoms, in which adjacent carbon atoms or adjacent carbon atoms via one carbon atom are bound to bonds a and b. Hydrocarbon groups in which carbon atoms are directly adjacent to each other are preferred.

Specific examples of $R_o$ include —CH$_2$CH$_2$—, —CH$_2$—CH$_2$—CH$_2$—, —CH(CH$_3$)CH$_2$—, —CH$_2$C(CH$_3$)$_2$—, —CH(CH$_3$)—CH(CH$_3$)—, —C(CH$_3$)$_2$C(CH$_3$)$_2$, —CH$_2$H$_5$)CH$_2$—, —CH(C$_2$H$_5$)CH(C$_2$H$_5$)—, —CH$_2$C(C$_2$H$_5$)$_2$—,

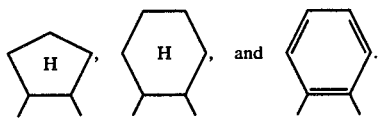

Preferable are —CH$_2$CH$_2$—, —CH$_2$C(CH$_3$)$_2$—,

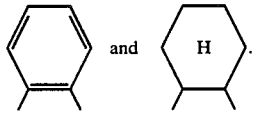

The Schiff base metal complex compound can be prepared by reacting an acyclic multidentate compound represented by the following formula (II)

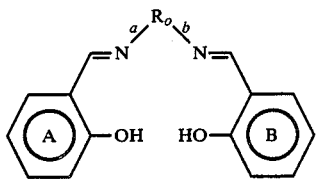

wherein rings A and B and $R_o$ are as defined above, with a transition metal of low valency selected from the group consisting of iron, cobalt, copper, nickel, manganese, chromium and zinc. Iron and cobalt are most preferred.

The term "polymeric ligand", as used in the present application, includes polymers containing a plurality of ligand groups which can coordinate with the central metal of the Schiff base metal complex of formula (I).

The ligand groups denote groups having at least one functional group selected from amino, amide, heteroring containing nitrogen atoms and azomethine groups. Typical examples of the ligand group are primary, secondary, tertiary amino, amide, pyridinyl, imidazolyl and azomethine.

Pyridinyl, imidazolyl, and azomethine group are especially preferred.

Examples of the polymer to which such ligand groups are bonded include polymers having the recurring unit selected from the class consisting

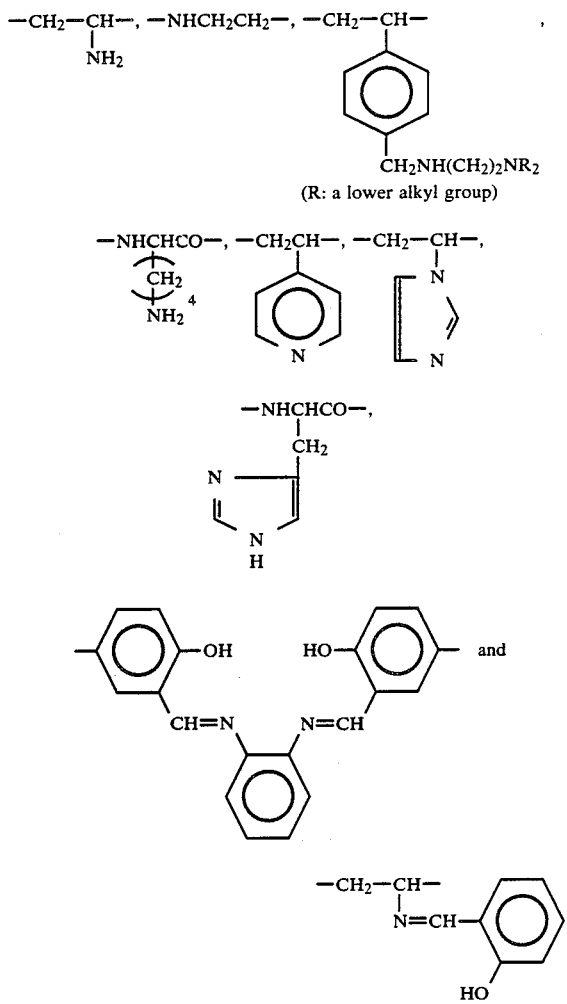

Vinyl polymer are preferred in view of the ease of production and the formability of coordinated bonds. Desirably, these polymers have film-forming property and generally have a number average molecular weight of 1,000 to 1,000,000, preferably 2,000 to 500,000.

A simple and convenient method of producing the polymeric ligand is to radical-polymerize an ethylenically unsaturated double bond-containing compound having the ligand group, such as vinylpyrimidine and vinylimidazole optionally together with another copolymerizable monomer.

In order to produce an ultrathin film having high gas separation selectivity, it is preferred to adjust the proportion of the ligand groups to at least one per 600 of the molecular weight of the polymer, preferably per 300 of the molecular weight of the polymer, most preferably per 150 of the molecular weight of the polymer. The molecular weight of the polymer is that of the polymeric ligand including the trunk polymer and the ligand groups.

Examples of the copolymerizable monomer are monomers which do not have the above ligand groups, such as acrylic acid, methacrylic acid, esters of these acids, and styrenes.

The amount of the copolymerizable monomer may be varied over a broad range depending upon the properties required of the resulting gas separation film of this invention, and cannot be generically defined. For example, when vinylpyridine or vinylimidazole is used as a monomer having a ligand group, it is preferred to use the above copolymerizable monomer jointly in an amount of not more than 50 mole %, preferably not more than 40 mole %, in order to increase the film-formability of the resulting polymeric ligand and the flexibility of the resulting film.

Preferably, the gas separation membrane of this invention can be prepared by interfacial reaction between the planar-type Schiff base metal complex compound of formula (I) and the polymeric ligand. The interfacial reaction of the metal complex with the polymeric ligand may be carried out in a mode of any of the combinations of liquid-solid, solid-liquid, liquid-liquid, gas-solid, etc. In order to form a uniform thin film, a combination which does not permit turbulance of the interface is desirably used. More specifically, the gas separation membrane of the invention can be produced, for example, by supporting the Schiff base metal complex compound on a solvent-resistant porous membrane such as a membrane of a cellulosic polymer, a fluorine-containing polymer, or an olefinic polymer, and bringing the supported Schiff base metal complex compound into contact with a solution of the polymeric ligand.

The resulting gas separation film of the invention in a form supported on the solvent-resistant porous membrane is used, for example, to concentrate a specific gaseous component selectively from a mixture of two or more gases. For example, it is very effective for production of oxygen-enriched air from atmospheric air or the separation of carbon monoxide-rich gas from water gas.

The following examples illustrate the invention more specifically without any intention of limiting the invention thereby.

The gas selectivity and gas permeability of the resulting film in the following examples were evaluated by measuring the permeation velocities of $O_2$ gas and $N_2$ gas respectively using a low vacuum-type apparatus (Rika Seiki, Inc.; model K-315 3BR-SSS) while maintaining the pressure on the upstream side at a value mentioned in each of the examples. The gas selectivity was calculated as the ratio of $O_2$-permeation velocity to $N_2$-permeation velocity.

REFERENTIAL EXAMPLE

Synthesis of a Schiff base metal complex compound:

9.8 g of 2-hydroxybenzaldehyde was dissolved in 200 ml of isopropanol, and a solution of 2.4 g of ethylenediamine in 200 ml of isopropanol was added dropwise. With stirring, the mixture was reacted for 2.5 hours under reflux. After the reaction mixture was allowed to cool, 4.5 g of potassium hydroxide dissolved in 80 ml of methanol was added. Subsequently, a solution of 10 g of cobalt acetate tetrahydrate in 145 ml of water was added, and the mixture was reacted for 2.5 hours under reflux. The reaction mixture was allowed to cool overnight, and the resulting precipitate was collected by filtration to obtain blackish red needles of bis(2hydroxybenzal)ethylenediimine cobalt [Co((Salen) for short].

In the IR spectrum of the product, an absorption assigned to C=N was observed in the vicinity of 1530 $cm^{-1}$. This led to that determination a Schiff base complex formed Elemental analysis of the product showed the following composition $$C:H:N:Co = 56.2:4.2:8.2:17.1 \ (\%)$$

which well corresponded to the following calculated value $$C_{16}H_{14}N_2O_2Co,$$

$$C:H:N:Co = 59.1:4.4:8.6:18.1 \ (\%).$$

EXAMPLE 1

A porous membrane of polytetrafluoroethylene (Fluoropore ®; average pore diameter 0.1 micrometer; made by Sumitomo Denko K. K.) was immersed in a saturated chloroform solution of Co(Salen), and ultrasonicated for 5 minutes to impregnate the solution uniformly. The membrane was then dried to give a membrane holding the metal complex. When the metal complex-bearing membrane was dipped in a 2 % by weight chloroform solution of a polymeric ligand (4-vinylpyridine/hexyl methacrylate copolymer with a 4-vinylpyridine unit content of 92 mole %; number average molecular weight 4,400), a permselective layer formed immediately. The resulting film showed high permselectivity as shown by its oxygen permeation velocity of $2.8 \times 10^{-7}$ $cm^3/cm^2 \cdot s \cdot cmHg$ and a selectivity of oxygen to nitrogen [$\alpha(O_2/N_2)$] of 7.0 with the pressure on the upstream side being 360 torr.

EXAMPLE 2

A polymeric complex membrane was prepared in the same way as in Example 1 except that to form an interface uniformly between the complex-bearing membrane and the polymeric ligand solution, methanol incapable of dissolving the complex was used as the solvent for the polymeric ligand solution. The resulting membrane showed high permselectivity as shown by its oxygen permeation velocity of $2.0 \times 10^{-8}$ $cm^3/cm^2 \cdot s \cdot cmHg$ and a selectivity of oxygen to nitrogen [$\alpha(O_2/N_2)$] of 8.6 with the pressure on the upstream side being 695 torr.

EXAMPLE 3

As in Example 1, the complex compound solution was impregnated in a Fluoropore ® filter (0 1 micrometer) and brought into contact with a glass plate, followed by drying. A complex-bearing membrane was obtained in which the complex was concentrated on the surface of the filter on the air side. A permselective layer was formed on the complex-bearing membrane in the same way as in Example 1, and the permselectivity of the resulting film was evaluated. It showed very high permselectivity as demonstrated by its oxygen permeation velocity of $1.26 \times 10^{-7}$ cm$^3$/cm$^2$.s.cmHg and a gas selectivity [$\alpha$(O$_2$/N$_2$)] of 10.3 with the pressure on the upstream side being 393 torr.

EXAMPLE 4

A porous regenerated cellulose membrane was immersed in a saturated chloroform solution of Co(Salen), and ultrasonicated for 5 minutes to impregnate the solution uniformly. Part of the surface of the porous membrane was then covered with a glass plate, and dried over the glass plate. There was obtained a complexbearing membrane in which the complex was uniformly impregnated in the evaporation surface of the porous membrane. A permselective layer was formed on the complex-bearing membrane as in Example 1, and the permselectivity of the resulting film was evaluated. It showed very high permselectivity as demonstrated by its oxygen permeation velocity of $9.61 \times 10^{-8}$ cm$^3$/cm$^2$.s.cmHg and a gas selectivity [$\alpha$(O$_2$)] of 22.3 with the pressure on the upstream side being 700 torr.

When a film having a permselective layer was produced separately by the above procedure, the film had high permselectivity as demonstrated by its oxygen permeation velocity of $3.12 \times 10^{-8}$ cm$^3$/cm$^2$.s.cmHg and a gas selectivity of [$\alpha$(O$_2$/N$_2$)] of 26.4 with the pressure on the upstream side being 100 torr.

EXAMPLE 5

A Fluoropore ® filter (0.1 micrometer) was set up in contact with a source of supply of a saturated chloroform solution of Co(Salen) to impregnate the complex compound solution in the open pores of the filter. A separately prepared film of a polymeric ligand (4-vinylpyridine/hexyl methacrylate copolymer; 4-vinylpyridine unit content 94.9 mole %; average molecular weight 4,500) was brought into intimate contact with the filter, hereby to form a permselective layer on the surface of the polymeric ligand film. This film showed a high permselectivity as demonstrated by its oxygen permeation velocity of $2.63 \times 10^{-8}$ cm$^3$/cm$^2$.s.cmHg and a gas selectivity [(O$_2$/N$_2$)] of 13.5 with the pressure on the upstream side being 762 torr.

EXAMPLE 6

A chloroform solution of a polymeric ligand (4-vinylpyridine/hexyl methacrylate copolymer; 4-vinylpyridine unit content 94.9 mole %; average molecular weight 4,500) was developed on a water surface kept at 5° C. to obtain a thin solid membrane. Five layers of this membrane were laminated to a porous polypropylene film (Celgard $^R$2400; a product of Polyplastics Co., Ltd.) to obtain a thin polymeric ligand composite film. When a saturated chloroform solution of Co(Salen) was impregnated into the composite film from the porous membrane side, a permselective layer immediately formed.

We claim:

1. A gas separation film comprising a solid permselective layer which is formed by reaction in situ of a Schiff base metal complex compound represented by the following formula (I)

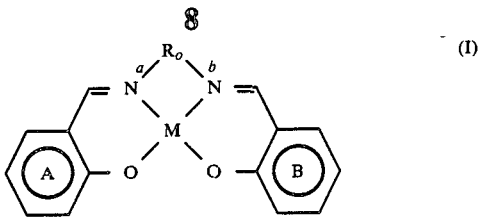

wherein rings A and B each represent an o-phenylene or o-naphthylene group which may be substituted by at least one group selected from the class consisting of halogen atoms and groups of the formula —X—R in which R represents a saturated or unsaturated aliphatic hydrocarbon group having not more than 22 carbon atoms and X represents a direct bond or a binding member between R and ring A or B, selected from the class consisting of —O—, —COO—, —NHCO— and —S—, R$_o$ represents a hydrocarbon group having not more than 6 carbon atoms in which adjacent carbon atoms or adjacent carbon atoms via one carbon atom are bound to bonds a and b, and M represent a metal selected from the group consisting of Fe, Co, Cu, Ni, Mn, Cr and Zn, with a polymeric ligand.

2. The gas separation film of claim 1 in which the polymeric ligand is a polymer containing an amino, amide, hetero-ring containing nitrogen atom and/or azomethine group.

3. The separation film of claim 1 in which the polymeric ligand is selected from homo- or co-polymers of vinylpyridine and homo- or co-polymers of vinyl imidazole.

4. The separation film of claim 1 in which the reaction in situ is an interfacial reaction in situ.

5. The gas separation film of claim 1 in which said polymeric ligand comprises recurring units selected from the group consisting of

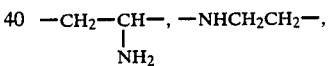

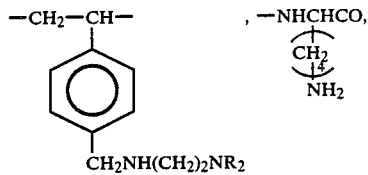

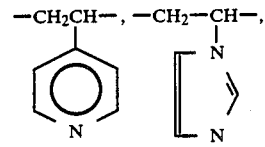

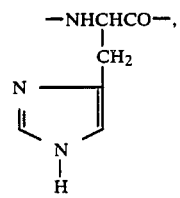

-continued

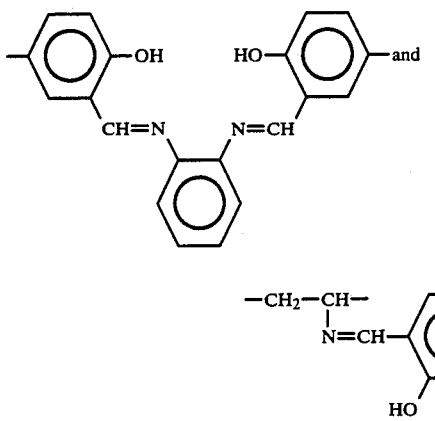

wherein R is a lower alkyl group.

6. The gas separation film of claim 1, wherein said polymeric ligand comprises a vinyl polymer.

7. The gas separation film of claim 6, wherein said vinyl polymer is film-forming.

8. The gas separation film of claim 6, wherein said vinyl polymer has a number average molecular weight of 1,000 to 1,000,000.

9. The gas separation film of claim 6, wherein said vinyl polymer has a number average molecular weight of , 2,000 to 500,000.

10. The gas separation film of claim 1, wherein R is an alkyl, alkenyl or alkynyl group.

11. The gas separation film of claim 10, wherein said alkyl group is selected from the group consisting of methyl, ethyl, propyl, isopropyl, butyl, isobutyl, tert-butyl, hexyl, octyl, 3-ethylhexyl, tetradecyl, pentadecyl, hexadecyl, heptadecyl, octadecyl and docosyl.

12. The gas separation film of claim 10, wherein said alkenyl group is selected from the group consisting of vinyl, allyl, cis-9-hexadecenyl and cis-9-cis-12-octadecadienyl.

13. The gas separation film of claim 10, wherein said alkynyl group is selected from the group consisting of propargyl and octadeca-1,12-diyl.

14. The gas separation film of claim 1, wherein $R_o$ has not more than 4 carbon atoms.

15. The gas separation film of claim 1, wherein $R_o$ is selected from the group consisting of —$CH_2CH_2$—, —$CH_2$—$CH_2$—$CH_2$—, —$CH(CH_3)CH_2$—, —$CH_2C(CH_3)_2$—, —$CH(CH_3)$—$CH(CH_3)$—, —$C(CH_3)_2$—$C(CH_3)_2$—, —$CH(C_2H_5)CH_2$—, —$CH(C_2H_5)CH(C_2H_5)$—, —$CH_2C(C_2H_5)_2$—,

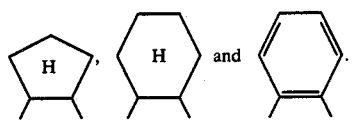

16. The gas separation film of claim 1, wherein $R_o$ is selected from the group consisting of —$CH_2CH_2$—, —$CH_2C(CH_3)_2$—,

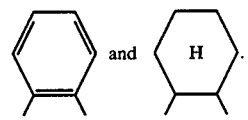

17. The gas separation film of claim 1, wherein M is Fe or Co.

* * * * *